United States Patent
Chen et al.

(10) Patent No.: US 7,968,618 B2
(45) Date of Patent: *Jun. 28, 2011

(54) ONE-COMPONENT DENTAL ADHESIVE COMPOSITIONS AND METHOD OF USE

(75) Inventors: Xiangxu Chen, Diamond Bar, CA (US); Xuejun Qian, Foothill Ranch, CA (US)

(73) Assignee: Kerr Corporation, Orange, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/835,422

(22) Filed: Jul. 13, 2010

(65) Prior Publication Data

US 2010/0278998 A1    Nov. 4, 2010

Related U.S. Application Data

(63) Continuation of application No. 11/321,489, filed on Dec. 29, 2005, now Pat. No. 7,767,731.

(51) Int. Cl.
*A61K 6/033* (2006.01)
*A61K 6/05* (2006.01)
*A61K 6/083* (2006.01)
*C08J 3/28* (2006.01)
*C08F 2/50* (2006.01)
*C08F 2/46* (2006.01)

(52) U.S. Cl. ........ 523/118; 523/109; 523/113; 523/115; 523/116; 523/117; 522/64; 522/71; 522/74; 522/83; 522/84; 522/85; 522/113; 522/114; 522/120; 522/115; 522/171; 522/178; 522/182

(58) Field of Classification Search ............. 522/64, 522/71, 74, 83, 84, 85, 113, 114, 120, 115, 522/171, 178, 182; 523/109, 113, 115, 116, 523/117, 118

See application file for complete search history.

(56) References Cited

U.S. PATENT DOCUMENTS

| | | |
|---|---|---|
| 4,872,936 A | 10/1989 | Engelbrecht |
| 5,130,347 A | 7/1992 | Mitra |
| 5,922,786 A | 7/1999 | Mitra et al. |
| 6,187,838 B1 | 2/2001 | Dickens |
| 6,288,138 B1 | 9/2001 | Yamamoto et al. |
| 6,353,041 B1 | 3/2002 | Qian |
| 6,387,979 B1 | 5/2002 | Hino |
| 6,387,982 B1 | 5/2002 | Blackwell |
| 6,750,268 B2 | 6/2004 | Hino |
| 6,812,266 B2 | 11/2004 | Klee et al. |
| 7,156,911 B2 | 1/2007 | Kangas et al. |
| 7,449,499 B2 * | 11/2008 | Craig et al. ............. 523/118 |
| 2003/0187092 A1 | 10/2003 | Fujiwara |
| 2003/0187094 A1 | 10/2003 | Klee et al. |
| 2004/0229973 A1 | 11/2004 | Sang et al. |
| 2004/0254261 A1 | 12/2004 | Kojima et al. |
| 2005/0175965 A1 | 8/2005 | Craig et al. |
| 2005/0175966 A1 | 8/2005 | Falsafi et al. |
| 2006/0069181 A1 | 3/2006 | Thalacker et al. |

FOREIGN PATENT DOCUMENTS

| EP | 1502569 A1 | 2/2005 |
|---|---|---|
| WO | 2005018581 A2 | 3/2005 |

OTHER PUBLICATIONS

Charlton, Dentin Bonding: Past and Present, General Dentistry 44 (6): pp. 498-507 (1996).
Optibond FL Product Summary from CureHunter [online], retrieved on Mar. 14, 2009 from Internet URL: http://www.curhunter.com/public/keywoodSummary 469607-OptiBone-FL.do.
Optibond All-In-One Technical Bulletin from Kerr [online] retrieved on Mar. 14, 2009 from the Internet URL http://www.kerrdental.com/index/cms-filesystem-action?file=/kerrdental-products-techspecs/optibondaiotechbulletin_122007.pdf, Dec. 2007.

* cited by examiner

*Primary Examiner* — Sanza L McClendon
(74) *Attorney, Agent, or Firm* — Wood, Herron & Evans, LLP

(57) ABSTRACT

A one-component self-etching self-priming dental adhesive composition is disclosed. The composition comprises glycerol phosphate di(meth)acrylate monomer, at least one monofunctional polymerizable monomer having just one ethylenically unsaturated group, at least one multi-functional polymerizable monomer having at least two ethylenically unsaturated groups, at least one aprotic solvent, at least one protic solvent, and at least one polymerization initiator.

20 Claims, No Drawings

ONE-COMPONENT DENTAL ADHESIVE COMPOSITIONS AND METHOD OF USE

RELATED APPLICATIONS

This application is a continuation of U.S. application Ser. No. 11/321,489, filed Dec. 29, 2005, now issued U.S. Pat. No. 7,767,731, the disclosure of which is hereby incorporated herein by reference in its entirety.

FIELD OF THE INVENTION

The invention relates to dental adhesives for tooth restoration.

BACKGROUND OF THE INVENTION

Resin based dental restorative materials are becoming the material of choice by dentists and patients due to desirable aesthetic properties. Contemporary dental adhesives evolve rapidly because patients want their teeth to be restored functionally, esthetically, and invisibly. The conventional form of dental adhesives requires three steps with successive applications of 1) an acid etchant that is normally phosphoric acid, 2) an adhesion promoting agent or primer, and 3) a bonding resin or adhesive. Between the first and second steps, water rinsing and drying are generally required. Between the second and third steps, drying is required. After all these three steps, light-curing is generally required to polymerize and harden the adhesive. This procedure is complex and, hence, technique-sensitive.

Efforts have been directed toward developing new types of dental adhesives to simplify the above dental adhesive application procedure. A simplified two-step procedure combines the primer and adhesive steps into one step. One of the commercialized products is Optibond Solo Plus® (Kerr Corporation, Orange Calif.). After total etch with a phosphoric acid etchant, followed by water rinsing and drying, Optibond Solo Plus® is then applied to tooth structures. Superior bonding strength is generated after appropriate light curing. This "etch & rinse" technique is widely accepted to be an effective approach to achieve efficient and stable dental bonding. Another simplified two-step procedure combines the acid etchant and primer steps into one step. The combination of acid etchant and primer is generally called a self-etching primer, and one of the commercialized products is Optibond Solo Plus Self-Etch Primer® (Kerr). After application of Optibond Solo Plus Self-Etch Primer on a tooth structure, drying, but no water rinsing, is required. Superior bonding strength is generated after appropriate application of Optibond Solo Plus® adhesive followed by light curing. A two-component one-step dental adhesive, Adper Prompt L-Pop® (3M ESPE, St. Paul Minn.), combines all three steps, but requires mixing of two separated parts before applying the adhesive on a tooth substrate.

U.S. Pat. No. 6,387,979 describes a bonding composition with high initial bonding strength and good bond durability. The composition is a mixture of a polymerizable compound having an acid group, a water-soluble film-forming agent, water, and a curing agent, in which the calcium salt of the acid is insoluble in water, and the film-forming agent is a polymerizable compound miscible with a physiological saline solution. The composition does not require any pre-treatment such as acid-etching or priming treatment. U.S. Published Patent Application No. 2003/0187092 describes a one-bottle dental bonding composition that is applied onto a tooth without any pretreatment of the tooth surface. The composition contains a radical polymerizable monomer with an acidic group and the composition is substantially free of water. U.S. Published Patent Application No. 2004/0229973 describes a two-part and one-part self-etching adhesive containing dipentaerythritol pentaacrylate phosphoric acid ester and 4,4'-oxydiphenylether-1,1',6,6'-tetracarboxylic acid-1,1'-(2-methacryloxy) dimethacrylate and/or 4-methacryloxyethyltrimellitic anhydride. U.S. Published Patent Application No. 2004/0254261 describes a one component dental composition in which a polymerizable compound having an acidic group is coexisted with a reducing agent such as a tertiary amine, water, and an alumina oxide powder.

SUMMARY OF THE INVENTION

The invention is directed to one-component self-etching self-priming dental adhesives that contain acidic polymerizable monomers. The composition comprises glycerol phosphate di(meth)acrylate monomer, at least one mono-functional polymerizable monomer having one ethylenically unsaturated group, at least one multi-functional polymerizable monomer having at least two ethylenically unsaturated groups, at least one aprotic solvent, at least one protic solvent, and at least one polymerization initiator, resulting in a self-etching dental adhesive composition.

DETAILED DESCRIPTION

The invention is directed to a self-etching and self-priming dental composition. The composition may be used as a dental adhesive and does not require pretreatment, such as acid etching and priming, of a tooth substrate.

The composition is a one component self-etching adhesive (SEA) that can etch and bond to a tooth structure by a simple one step application and without premixing. The composition provides an effective and durable bond to a tooth substrate. Only a single step dental adhesion process is needed that does not require separate etching with an acid gel and/or priming with a hydrophilic primer. In one embodiment, shear bond strength of at least 10 MPa is achieved using the inventive adhesives to bond dental composites onto tooth structures.

The one-component self-etching dental adhesive composition comprises
 a) glycerol phosphate di(meth)acrylate monomer;
 b) at least one mono-functional polymerizable monomer having just one ethylenically unsaturated group;
 c) at least one multi-functional polymerizable monomer having at least two ethylenically unsaturated groups;
 d) at least one aprotic solvent;
 e) at least one protic solvent; and
 f) at least one polymerization initiator.

The inventive composition achieves good adhesion to a tooth structure, both dentin and enamel, without the need for separate etching and priming. This composition effectively and simultaneously etches, primes, and bonds to a tooth structure.

Component (a) is glycerol phosphate di(meth)acrylate{(meth)acrylate=acrylate or methacrylate} monomer having two polymerizable (meth)acrylate groups and a covalently linked phosphoric acid group. Glycerol phosphate di(meth)acrylate is an acidic monomer that achieves effective etching and adhesion to a tooth structure. In the inventive composition, the concentration of glycerol phosphate di(meth)acrylate monomer should not be above about 60% w/w because properties and shelf life are negatively affected by high acidity. High acidity may also cause substantial degradation of initiator systems that involve amines because acidic monomers may protonate amines that are used as a co-initiator for camphorquinone (CQ). In one embodiment, the amount of glycerol phosphate di(meth)acrylate in the composition is in the range of about 1% w/w to about 60% w/w. In another embodiment, the amount of glycerol phosphate di(meth) acrylate in the composition is in the range of about 3% w/w to about 40% w/w. In another embodiment, the amount of glycerol phosphate di(meth)acrylate in the composition is in the range of about 5% w/w to about 20% w/w.

In addition to glycerol phosphate di(meth)acrylate, other acidic compound(s) having at least one acidic functional group can optionally be included in the composition. Acidic functional groups include, but are not limited to, phosphoric acid, a phosphoric acid derivative, phosphonic acid, a phosphonic acid derivative, carboxylic acid, carboxylic acid anhydride, sulfonic acid, sulfinic acid. Unless stated otherwise, a derivative includes a salt or ester of the respective acid. Examples of these acidic compounds include, but are not limited to, maleic acid, itaconic acid, methacrylic acid, acrylic acid, tartaric acid, ethylenediaminetetraacetic acid (EDTA), EDTA salt, citric acid, a homopolymer or copolymer of an α,β-unsaturated carboxylic acid such as poly (acrylic acid), copolymer of acrylic acid such as poly(acrylic acid-maleic acid) copolymer or poly(acrylic acid-itaconic acid) copolymer or poly(acrylic acid-maleic acid-itaconic acid) copolymer, polymerizable homopolymer or copolymer of an α,β-unsaturated carboxylic acid such as (meth)acrylated poly(acrylic acid), (meth)acrylated poly(acrylic acid) copolymer such as (meth)acrylated poly(acrylic acid-maleic acid) copolymer or (meth)acrylated poly(acrylic acid-maleic acid-itaconic acid) copolymer, maleic anhydride, trimellitic anhydride, 4-META (4-methacryloxyethyltrimellitic anhydride), any addition product of mono- or di-anhydride compound with a hydroxyalkylmethacrylate compound such as PM-HEMA (addition product of pyromellitic acid anhydride and 2-hydroxyethyl methacrylate), PM-GDM (addition product of pyromellitic acid anhydride and glycerol dimethacrylate), BTDA-HEMA (addition product of 3,3',4,4'-benzophenonetetracarboxylic dianhydride and hydroxyethyl methacrylate), and PA-HEMA (addition product of phthalic anhydride and hydroxyethyl methacrylate), MA-GDM (addition product of maleic anhydride and glycerol dimethacrylate), sulfuric acid, alkyl sulfonic acid, aromatic sulfonic acid, alkyl sulfinic acid, aromatic sulfinic acid, phosphoric acid, pyrophosphoric acid, monoalkyl phosphate, dialkyl phosphate, aryl alkyl phosphate, aryl phosphate, phenyl-P (phenyl methacryloxyethyl phosphate), PENTA-P (dipentaerithritol pentaacrylate phosphate), MDP (methacryloyloxydecyl phosphate), HEMA-P (hydroxyethylmethacrylate phosphate), HEA-P (hydroxyethylacrylate phosphate), bis (HEMA)-P {bis(hydroxyethylmethacrylate) phosphate}, bis (HEA)-P {bis(hydroxyethylacrylate) phosphate}, bis(meth) acryloxypropyl)phosphate, and combinations of these.

Component (b) is one or more mono-functional polymerizable monomer(s) having only one ethylenically unsaturated group. The ethylenically unsaturated group may be an acrylate, methacrylate, or vinyl group. Mono-functional monomers include, but are not limited to, methyl (meth)acrylate, ethyl (meth)acrylate, propyl (meth)acrylate, butyl (meth) acrylate, hydroxyethyl (meth)acrylate, hydroxypropyl (meth)acrylate, glycerol mono(meth)acrylate, polyethyleneglycol mono-(meth)acrylate, polypropyleneglycol mono-(meth)acrylate, polytetramethyleneglycol mono-(meth)acrylate, or combinations of these. In one embodiment, the monofunctional monomers include methyl (meth)acrylate, hydroxyethyl (meth)acrylate, and/or glycerol mono(meth) acrylate. In one embodiment, the amount of mono-functional monomer(s) in the composition is in the range of about 1% w/w to about 60% w/w. In another embodiment, the amount of mono-functional monomer(s) in the composition is in the range of about 2% w/w to about 45% w/w. In another embodiment, the amount of mono-functional monomer(s) in the composition is in the range of about 5% w/w to about 30% w/w.

Component (c) is one or more multi-functional polymerizable monomer(s) having at least two ethylenically unsaturated groups. Multi-functional monomers can form a cross linking network with polymerization that makes the dental adhesive layer durable. Multi-functional monomers include, but are not limited to, glycerol di(meth)acrylate, glycerol tri(meth)acrylate, 2,2-bis[4-(2-hydroxy-3-methacryloylpropoxy)-phenyl]-propane (BisGMA), urethane di(meth)acrylate, ethoxylated bisphenol A dimethacrylate (EBPADMA-n where n=total number of moles of ethylene oxide in the molecule, as only one example, n=2-20 units), ethylene glycol di(meth)acrylate, neopentyl glycol di(meth)acrylate, tetraethylene glycol di(meth)acrylate, triethylene glycol di(meth)acrylate, diethylene glycol di(meth)acrylate, 1,3-butylene glycol di(meth)acrylate, cyclohexane dimethanol di(meth)acrylate, 1,6-hexanediol di(meth)acrylate, 1,4-butanediol dimethacrylate, propoxylated glyceryl tri(meth) acrylate, polyethyleneglycol di-(meth)acrylate, polypropyleneglycol di-(meth)acrylate, polytetramethyleneglycol di-(meth)acrylate, trimethylolpropane tri(meth)acrylate, ethoxylated trimethylolpropane tri(meth)acrylate, tris (2-hydroxy ethyl) isocyanurate tri(meth)acrylate, pentaerythritol di(meth)acrylate, pentaerythritol tri(meth)acrylate, pentaerythritol tetra(meth)acrylate, dipentaerythritol penta (meth)acrylate, multifunctional aliphatic urethane (meth) acrylate, multifunctional aromatic urethane (meth)acrylate or combinations of these. In one embodiment, the multi-functional monomers include glycerol di(meth)acrylate, glycerol tri(meth)acrylate, 2,2-bis[4-(2-hydroxy-3-methacryloylpropoxy)-phenyl]-propane (BisGMA), urethane di(meth)acrylate, trimethylolpropane tri(meth)acrylate, ethoxylated trimethylolpropane tri(meth)acrylate, and/or dipentaerythritol penta(meth)acrylate. In one embodiment, the amount of multi-functional monomer(s) in the composition is in the range of about 1% w/w to about 70% w/w. In another embodiment, the amount of multi-functional monomer(s) in the composition is in the range of about 5% w/w to about 50% w/w. In another embodiment, the amount of multi-functional monomer(s) in the composition is in the range of about 10% w/w to about 40% w/w.

Solvents [components (d) and (e)] are needed to dissolve monomers, initiators and other necessary ingredients. The solvents used in the inventive composition are a combination of protic [component (e)] and aprotic [component (d)] solvents. A protic solvent is any solvent that carries hydrogen attached to, as in a hydroxyl group, or nitrogen as in an amine group. Protic solvents include, but are not limited to, water, ethyl alcohol, propyl alcohol, isopropyl alcohol, butyl alcohol and tert-butyl alcohol. In one embodiment, the protic solvents are water and/or ethyl alcohol. The presence of protic solvents can facilitate the etching of tooth structures and hence improve bonding properties. In the inventive composition, the presence of water is preferred. In one embodiment, the amount of protic solvent(s) in the composition is in the range of about 1% w/w to about 60% w/w. In another embodiment, the amount of protic solvent(s) in the composition is in the range of about 3% w/w to about 50% w/w. In another embodiment, the amount of protic solvent(s) in the composition is in the range of about 5% w/w to about 40% w/w. An aprotic solvent is any solvent that does not carry hydrogen attached to oxygen or nitrogen. Without the presence of aprotic solvents, the inventive composition does not have enough stability to achieve a desired shelf life. Aprotic solvents include, but are not limited to, acetone, methyl ethyl ketone, ethyl acetate, tetrahydrofuran and diethyl ether. In one embodiment, the aprotic solvent is acetone. In one embodiment, the amount of aprotic solvent(s) in the composition is in the range of about 5% w/w to about 80% w/w. In another embodiment, the amount of aprotic solvent(s) in the composition is in the range of about 10% w/w to about 70% w/w. In another embodiment, the amount of aprotic solvent(s) in the composition is in the range of about 20% w/w to about 60% w/w. In one embodiment, all solvents are removed by drying the applied composition with compressed air from a dental air syringe before a dental curing light is used to cure the composition. In another embodiment, solvents are only partially removed by drying the applied composition with compressed air from a dental air syringe before a dental curing light is used to cure the composition. The air drying time may be between 1 second to 40 seconds.

Component (f) is a polymerization initiator for initiating polymerization of the composition and causing hardening of the composition. In one embodiment, the amount of polymerization initiator(s) in the composition is in the range of about 0.01% w/w to about 10% w/w. In another embodiment, the amount of polymerization initiator(s) in the composition is in the range of about 0.05% w/w to about 8% w/w. In another embodiment, the amount of polymerization initiator(s) in the composition is in the range of about 0.1% w/w to about 5% w/w. In one embodiment, the polymerization initiator is a photo-initiator that initiates polymerization of the composition through light activation with a dental curing light capable of generating ultraviolet and/or visible light. A photo-initiator usually comprises a photo-sensitizer and a reducing agent. Photo-initiators/sensitizers include, but are not limited to, camphorquinone (CQ), phenathrenequinone, 4,4'-bis(dimthylamino)benzophenone, and 4,4-bis(diethylamino) benzophenone. CQ has absorption of visible light and in one embodiment is used. Amines, especially tertiary amines, can be used as reducing agents for CQ to co-initiate free radical polymerization. Tertiary amines include, but are not limited to, ethyl-4-(N,N-dimethylamino) benzoate (EDMAB), 2-ethylhexyl-4-(N,N-dimethylamino) benzoate (ODMAB), 4-dimethylamino-benzophenone (DMABP), p-dimethylamino benzoic acid (DMABA), p-(dimetnylamino) benzonitrile (DMABCN), p-(dimetnylamino) benzaldehyde, 4'-morpholino-acetophenone, 4'-morpholino-benzophenone, p-(dimethylamino) acetophenone, 4,4'-bis(dimethylamino) benzophenone, 4,4'-bis(diethylamino) benzophenone and dimethylaniline. In one embodiment, among these tertiary amines, EDMAB, ODMAB, DMABP, DMABA and/or DMABCN are used. Other reducing agents for camphorquinone include, but are not limited to, chemical compounds with urethane and benzhydyl groups.

In one embodiment, phosphine oxides, including mono-acyl and multi-acyl phosphine oxide, are used as photoinitiators. Phosphine oxides themselves can initiate free radical polymerizations under ultraviolet (UV) and/or visible irradiation generated by a typical dental curing device. Examples of phosphine oxides include, but are not limited to, bis(2,4,6-trimethylbenzoyl)-phenyl phosphine oxide (Irgacure 819, Ciba Specialty Chemicals, Basel Switzerland), bis(2,6-dimethoxybenzoyl)-(2,4,4-trimethylpentyl) phosphine oxide (CGI 403, Ciba Specialty Chemicals) and ethyl 2,4,6-trimethylbenzoyl-phenyl phosphine oxide (LUCIRIN® LR8893X, BASF Corp., Charlotte N.C.). In one embodiment, combinations of two or more phosphine oxides are used.

In one embodiment, fluoron and pyronin derivatives initiate free radical polymerizations together with amines and iodonium synergists under UV and/or visible irradiations generated by a typical dental curing device. Examples of fluoron and pyronin derivatives include, but are not limited to, 5,7-diiodo-3-butoxy-6-fluorone (H-Nu 470, Spectra Group Ltd., Millbury Ohio). Other examples of fluoron and pyronin derivatives that can initiate free radical polymerizations are described in U.S. Pat. Nos. 5,623,080 and 5,451,343, each of which are expressly incorporated by reference herein in its entirety.

Fillers can also be incorporated into the inventive compositions. Fillers enhance mechanical properties of the composition, reduce polymerization shrinkage, improve rheological and handling properties of composition, and increase radiopacity of the composition for ease in detection of gaps or voids. Examples of fillers include, but are not limited to, inorganic metal, salt, oxide, nitride, silicate glass, aluminosilicate glass, aluminoborosilicate glass, fluoroaluminosilicate glass, quartz, colloidal silica, fumed silica, precipitated silica, zirconia silica, polymeric filler and/or polymerized composite fillers with inorganic particles. In one embodiment, fumed silica, colloidal silica and/or precipitated silica are used. Examples of colloidal and fumed silicas include, but are not limited to, AEROSIL® series and AERODISP® series (both from Degussa, Ridgefield Park N.J.) and Cab-O-Sil® series (Cabot Corp., Tuscola Ill.). AEROSIL® series include, but are not limited to, AEROSIL® 130, 150, 200, 300, 380, R202, R805, R972, OX-50, and OX200 silica. AERODISP® series include, but are not limited to, AERODISP® W1714, W1824, W1836, W630, W7512S and W7520, all of which are water-based dispersions. Cab-O-Sil® series include, but are not limited to, Cab-O-Sil® M5, LM-150, TS-720, TS-610 and TS-530. The filler also includes nanoparticles such as those obtained through a sol-gel process. Examples include those disclosed in U.S. Pat. Nos. 4,567,030 and 5,609,675, each of which is expressly incorporated by reference herein in its entirety. In one embodiment, mixtures of different fillers are used. For inorganic fillers, the surface of the filler may be treated or coated with a coupling agent, such as gamma-methacryloyloxypropyltrimethoxy-silane (MPTMS), that enhances the interfacial bonding between the filler and resin matrix and improves mechanical properties. Both micrometer size and nanometer size fillers can be used. In one embodiment, fumed silica fillers are used. In one embodiment, the amount of filler, if present, is up to about 40 parts by weight of the composition. In another embodiment, the amount of filler, if present, is up to about 20 parts by weight of the composition.

Fluoride releasing and/or anti-microbial agents can also be incorporated in the inventive composition, for example, to prevent secondary caries and reduce plaque formation. The fluoride releasing agent may be fillers or ethylenically unsaturated monomers. The fluoride releasing fillers include, but are not limited to, sodium hexafluorosilicate, zinc hexafluorosilicate, strontium hexafluorosilicate, sodium fluoride, potassium fluoride, calcium fluoride, strontium fluoride, magnesium fluoride and water-soluble inorganic complex fluoride described in U.S. Pat. No. 5,824,720, which is expressly incorporated by reference herein in its entirety. Ethylenically unsaturated fluoride releasing agents include, but are not limited to, fluoride-containing complexes of Lewis bases and boron trifluoride described in U.S. Pat. No. 4,772, 325 and chelating monomers described in U.S. Pat. No. 6,703,518, each of which is expressly incorporated by reference herein in its entirety. Anti-microbial agents include, but are not limited to, benzalkonium chloride, triclosan, alkyl 4-hydroxybenzoate, silicate glass powder containing silver and/or zinc, and/or zeolite powder containing silver and/or zinc. Examples of commercially available antimicrobial additives are IRGAGUARD® B 1000 (triclosan), IRGAGUARD® B 5000 (silver-zinc zeolite) and B 6000 (silver glass/zeolite) and 7000 (silver-zinc glass). All IRGAGUARD® products are from Ciba Specialty Chemicals.

In one embodiment, to obtain a chemically stable composition that has a shelf-life of at least one year, and in one embodiment of at least two years at room temperature (e.g., about 22° C.), a stabilizer is used. Stabilizers include, but are not limited to, 3,5-di-tert-butyl-4-hydroxytoluene (BHT) and hydroquinone monomethyl ether (MEHQ). The stabilizer may be present in the composition at a concentration between about 0.0001% w/w and 5% w/w.

The inventive composition can optionally contain additives including, but not limited to, curing indicators, non-reactive diluents, ultraviolet absorbers, photochromic agents, and/or photobleachable agents.

The inventive composition can be packaged in a bottle or a single-dose device, container, vial, etc.

The invention also includes a method for using the inventive composition. The method includes the steps of (a) preparing the tooth by removing carious dentition and/or rendering it suitable for receiving a prosthetic device; (b) placing at least one application of the inventive adhesive composition on the prepared dentition; (c) completely or partially removing the solvent component of the composition by air drying the applied adhesive composition; (d) polymerizing the adhesive composition by photo-curing the composition; and (e) either (i) placing a composite resin on the photo-cured adhesive composition and subsequently curing/hardening the composite resin; or (ii) adhering a prosthetic device onto the adhesive-covered tooth/teeth with a cement or composite resin and subsequently curing/hardening the cement or composite resin. The prosthetic device can be a veneer, an inlay, an onlay, a crown, crowns and bridge, or an endodontic post. Curing the composite resin or cement can be by self-curing, photo-curing, or dual-curing (i.e. the combination of self-curing and photo-curing).

The following examples illustrate how the current invention may be applied and do not limit the scope of the invention.

EXAMPLES

In the examples the following materials were used:
BHT: 2,6-di-(tert-butyl)-4-methylphenol
Bis-GMA: 2,2-bis[4-(2-hydroxy-3-methacryloylpropoxy)-phenyl]-propane
CQ: camphorquinone
DPPA: dipentaerythrytol pentaacrylate
EDMAB: ethyl-4-(N,N-dimethylamino) benzoate
GDM: glycerol dimethacrylate
GPDM: glycerol phosphate dimethacrylate
HEMA: hydroxyethyl methacrylate
MEPA: methacryloxyethylpyromellitic acid
ODMAB: 2-ethylhexyl-4-(N,N-dimethylamino) benzoate
OX-50: fumed silica or colloidal silica sold by Degussa
PMGDM: pyromellitic glycerol dimethacrylate
TMPTMA: trimethylolpropane trimethacrylate
TS-530: surface treated fumed silica or colloidal silica sold by Cabot Corp
ST-ABS: aluminoborosilicate glass with a mean particle size of 1 micron and surface treated with γ-methacryloyloxypropyltrimethoxysilane
ST-OX50: OX-50 surface treated with γ-methacryloyloxypropyltrimethoxysilane Example 1

A one-component SEA composition was prepared that comprised 11.9 parts by weight of GPDM, 1.7 parts by weight of GDM, 13.6 parts by weight of Bis-GMA, 8.5 parts by weight of HEMA, 0.5 parts by weight of CQ, 0.94 parts by weight of ODMAB, 0.03 parts by weight of BHT, 5.1 parts by weight of ethyl alcohol, 37.4 parts by weight of acetone, 11.9 parts by weight of de-ionized water, 12.0 parts by weight of ST-ABS, 3.0 parts by weight of ST-OX50.

The composition was then used to bond composites to dentin and enamel. Before application of the composition, human dentin surfaces were polished by 600 grid sand paper and bovine enamel surfaces were cleaned by polishing with pumice flour. Two coats of the composition were applied on dentin or enamel surfaces and each coat was applied with 20 seconds agitation. The composition was then dried with compressed air from a dental air syringe for about 5 seconds to about 15 seconds. The composition was then polymerized by photo-curing for 20 seconds using a dental curing light (Optilux® 501, Kerr Calif.). Bonding jigs (Ultradent®, South Jordan Utah) with cylindrical molds (diameter=2.38 mm) were securely placed over the substrates, and a dental restorative composite (Herculite XRV™, Kerr Calif.) was filled followed by light curing with a dental curing device. For both dentin and enamel bonding, four specimens were prepared.

After the bonded specimen had been stored in water at 37° C. for about 20 hours, dentin and enamel shear bond strength was measured and was 32.06±4.69 MPa and 17.02±6.45 MPa, respectively. The composition was also subjected to accelerated aging. The composition was stored at 42° C. for eight weeks and bonding tests on dentin and enamel were conducted using the aged composition following the same bonding procedure described above. After the bonded specimen had been stored in water at 37° C. for about 20 hours, dentin and enamel shear bond strength was measured and was 18.97±8.54 MPa and 22.51±6.65 MPa, respectively.

Example 2

A one-component SEA composition was prepared that comprised 6 parts by weight of GPDM, 6 parts by weight of GDM, 16 parts by weight of Bis-GMA, 10 parts by weight of HEMA, 0.8 parts by weight of CQ, 1.1 parts by weight of ODMAB, 0.04 parts by weight of BHT, 48 parts by weight of acetone, 12 parts by weight of de-ionized water.

The composition was then used to bond composites to dentin and enamel. The same bonding procedure described in Example 1 was followed. After the bonded specimen had been stored in water at 37° C. for about 20 hours, dentine and enamel shear bond strength were measured and were 18.91±8.74 MPa and 15.42±1.27 MPa, respectively. The composition was also subjected to accelerated aging. The composition was stored at 42° C. for six weeks and bonding tests on dentin and enamel were conducted using the aged composition following the same procedure described above. After the bonded specimen had been stored in water at 37° C. for about 20 hours, dentine and enamel shear bond strength were measured and were 23.28±1.93 MPa and 20.35±5.57 MPa, respectively. Bonding tests on dentin and enamel of the composition stored at 42° C. for eight weeks were also conducted using the same procedure described above. After the bonded specimen had been stored in water at 37° C. for about 20 hours, dentine and enamel shear bond strength was measured and were 28.99±5.83 MPa and 22.43±4,66 MPa, respectively.

Example 3

A one-component SEA composition was prepared that comprised 9 parts by weight of GPDM, 6 parts by weight of GDM, 12 parts by weight of Bis-GMA, 6 parts by weight of HEMA, 6 parts by weight of PMGDM, 0.8 parts by weight of CQ, 1.1 parts by weight of ODMAB, 0.04 parts by weight of BHT, 46 parts by weight of acetone, 14 parts by weight of de-ionized water.

The composition was then used to bond composite to dentin and enamel. The same bonding procedure described in Example 1 was followed. After the bonded specimen had been stored in water at 37° C. for about 20 hours, dentine and enamel shear bond strength were measured and were 23.84±7.04 MPa and 23.99±4.35 MPa, respectively. The composition was also subjected to accelerated aging. The composition was stored at 42° C. for five weeks and bonding tests on dentin and enamel were conducted using the aged composition following the same procedure described above. After the bonded specimen had been stored in water at 37° C. for about 20 hours, dentine and enamel shear bond strength were measured and were 18.99±6.92 MPa and 11.43±2.76 MPa, respectively.

Example 4

A one-component SEA composition was prepared that comprised 6 parts by weight of GPDM, 4 parts by weight of GDM, 14 parts by weight of Bis-GMA, 6 parts by weight of TMPTMA, 8 parts by weight of HEMA, 0.6 parts by weight of CQ, 1.0 parts by weight of ODMAB, 0.04 parts by weight of BHT, 48.0 parts by weight of acetone, 12 parts by weight of de-ionized water.

The composition was then used to bond composite to dentin and enamel. The same bonding procedure described in Example 1 was followed. After the bonded specimen had been stored in water at 37° C. for about 20 hours, dentine and enamel shear bond strength were measured and were 27.96±4.53 MPa and 23.68±2.58 MPa, respectively. The composition was also subjected to accelerated aging. The composition was stored at 42° C. for five weeks and bonding tests on dentin and enamel were conducted using the aged composition following the same procedure described above. After the specimen had been stored in water at 37° C. for about 20 hours, dentine and enamel shear bond strength were measured and were 28.83±2.61 MPa and 21.32±5.36 MPa, respectively. Bonding tests on dentin and enamel of the composition stored at 42° C. for eight weeks were also conducted using the same procedure described above. After the bonded specimen had been stored in water at 37° C. for about 20 hours, dentine and enamel shear bond strength were measured and were 23.41±7.54 MPa and 22.49±2.04 MPa, respectively.

Example 5

A one-component SEA composition was prepared that comprised 8 parts by weight of GPDM, 2 parts by weight of GDM, 16 parts by weight of Bis-GMA, 4 parts by weight of HEMA, 12 parts by weight of MEPA, 0.6 parts by weight of CQ, 1.1 parts by weight of ODMAB, 0.04 parts by weight of BHT, 44.0 parts by weight of acetone, 10 parts by weight of ethanol, 10 parts by weight of de-ionized water.

The composition was then used to bond composite to dentin and enamel. The same bonding procedure described in Example 1 was followed. After the bonded specimen had been stored in water at 37° C. for about 20 hours, dentine and enamel shear bond strength were measured and were 22.57±1.72 MPa and 20.15±3.21 MPa, respectively. The composition was also subjected to accelerated aging. The composition was stored at 42° C. for four weeks and bonding tests on dentin and enamel were conducted using the aged composition following the same procedure described above. After the specimen had been stored in water at 37° C. for about 20 hours, dentine shear bond strength were measured and were 14.18±5.16 MPa. Bonding tests on dentin and enamel of the composition stored at 42° C. for eight weeks were also conducted using the same procedure described above. After the bonded specimen had been stored in water at 37° C. for about 20 hours, dentine shear bond strength was measured and was 10.96±3.54 MPa.

Example 6

A one-component SEA composition was prepared that comprised 18.7 parts by weight of GPDM, 3.4 parts by weight of GDM, 20.4 parts by weight of Bis-GMA, 12.8 parts by weight of HEMA, 0.68 parts by weight of CQ, 1.4 parts by weight of ODMAB, 0.034 part by weight of BHT, 22.1 parts by weight of ethanol alcohol, 6.0 parts by weight of de-ionized water, 12.0 parts by weight of ST-ABS, 3.0 parts by weight of ST-OX50.

The composition was then used to bond the composite to dentin. The same bonding procedure described in Example 1 was followed. After the bonded specimen had been stored in water at 37° C. for about 20 hours, dentine and enamel shear bond strength were measured and were 21.40±2.42 and 11.28±5.10 MPa, respectively. The composition was also subjected to accelerated aging. The composition was stored at 42° C. for four weeks and then bonding tests on dentin and enamel were conducted using the aged composition following the same procedure described above. After the bonded specimen had been stored in water at 37° C. for about 20 hours, dentine and enamel shear bond strength were measured and were 21.60±3.45 MPa and 5.76±4.88 MPa, respectively.

The above examples are for illustration only, and should not be construed to limit the scope of the invention. Other variations or embodiment will also be apparent to one skilled in the art from the description and examples. Thus, the embodiments are not to be construed as limiting the scope of the claimed invention.

What is claimed is:

1. A one-component self-etching dental adhesive composition comprising
   a) glycerol phosphate di(meth)acrylate monomer,
   b) at least one mono-functional polymerizable monomer having one ethylenically unsaturated group,
   c) at least one multi-functional polymerizable monomer having at least two ethylenically unsaturated groups,
   d) acetone,
   e) at least one protic solvent selected from water or ethanol, and
   f) at least one polymerization initiator,
resulting in a self-etching dental adhesive composition.

2. The composition of claim 1 wherein the concentration of glycerol phosphate di(meth)acrylate ranges from about 1% w/w to about 60% w/w.

3. The composition of claim 1 wherein the concentration of glycerol phosphate di(meth)acrylate ranges from about 3% w/w to about 40% w/w.

4. The composition of claim 1 wherein the concentration of the mono-functional polymerizable monomer(s) ranges from about 1% w/w to about 60% w/w.

5. The composition of claim 1 wherein the concentration of the multi-functional polymerizable monomer(s) ranges from about 1% w/w to about 70% w/w.

6. The composition of claim 1 wherein the concentration of the acetone ranges from about 5% w/w to about 80% w/w.

7. The composition of claim 1 wherein the concentration of the acetone ranges from about 10% w/w to about 70% w/w.

8. The composition of claim 1 wherein the concentration of the protic solvent(s) ranges from about 1% w/w to about 60% w/w.

9. The composition of claim 1 wherein the concentration of the protic solvent(s) ranges from about 3% w/w to about 50% w/w.

10. The composition of claim 1 wherein the concentration of the polymerization initiator(s) ranges from about 0.01% w/w to about 10% w/w.

11. The composition of claim 1 wherein the mono-functional polymerizable monomer is hydroxyethyl (meth)acrylate.

12. The composition of claim 1 wherein the protic solvent is water and ethanol.

13. The composition of claim 1 wherein the polymerization initiator comprises a photo-sensitizer and a reducing agent.

14. The composition of claim 13 wherein the photo-sensitizer is camphorquinone, and the reducing agent is a tertiary amine.

15. The composition of claim 14 wherein the tertiary amine is selected from at least one of ethyl-4-(N,N-dimethylamino) benzoate, 2-ethylhexyl-4-(N,N-dimethylamino)benzoate, 4-dimethylamino-benzophenone, p-dimethylamino benzoic acid, or p-dimethylamino benzonitrile.

16. The composition of claim 1 wherein the polymerization initiator is a phosphine oxide selected from at least one of mono-acyl phosphine oxide or bis-acyl phosphine oxide.

17. The composition of claim 1 further comprising at least one finely divided filler.

18. A method for using a dental adhesive composition comprising
(a) providing to a prepared dentition surface at least one application of a one-component self-etching dental adhesive composition comprising glycerol phosphate di(meth)acrylate monomer, at least one mono-functional polymerizable monomer having one ethylenically unsaturated group, at least one multi-functional polymerizable monomer having at least two ethylenically unsaturated groups, acetone, at least one protic solvent selected from water or ethanol, and at least one polymerization initiator;
(b) drying the applied composition to at least partially remove the solvent from the composition;
(c) photo-curing the dried composition to result in a polymerized composition;
(d) thereafter either (i) providing a composite resin to the polymerized composition and subsequently curing/hardening the composite resin; or (ii) adhering a prosthetic device on the composition-covered tooth with a cement or composite resin and subsequently curing/hardening the cement or composite resin.

19. The method of claim 18 wherein prepared dentition comprises carious dentition removal, rendering a tooth for a prosthetic device, or combinations thereof.

20. The method of claim 1 wherein the composition further comprises at least one of a finely divided filler, a fluoride releasing agent, a stabilizer, or an antimicrobial agent.

* * * * *